(12) United States Patent
Brinkman et al.

(10) Patent No.: US 11,389,057 B2
(45) Date of Patent: Jul. 19, 2022

(54) VISION MEASUREMENT DEVICE AND METHOD OF MEASURING VISION USING THE SAME

(71) Applicant: Essilor International, Charenton-le-Pont (FR)

(72) Inventors: Ross Brinkman, Chicago, IL (US); Paul Hatch, Chicago, IL (US); Patricia Howes, Chicago, IL (US); Eric Wiegmann, Chicago, IL (US); Andreas Bell, Chicago, IL (US)

(73) Assignee: Essilor International, Charenton-le-Pont (FR)

( * ) Notice: Subject to any disclaimer, the term of this patent is extended or adjusted under 35 U.S.C. 154(b) by 206 days.

(21) Appl. No.: 16/644,773

(22) PCT Filed: Sep. 26, 2018

(86) PCT No.: PCT/EP2018/076053
§ 371 (c)(1),
(2) Date: Mar. 5, 2020

(87) PCT Pub. No.: WO2019/063584
PCT Pub. Date: Apr. 4, 2019

(65) Prior Publication Data
US 2021/0076929 A1    Mar. 18, 2021

(30) Foreign Application Priority Data
Sep. 28, 2017   (EP) .................................... 17306290

(51) Int. Cl.
*A61B 3/032*    (2006.01)
*A61B 3/00*     (2006.01)
(Continued)

(52) U.S. Cl.
CPC ............ *A61B 3/032* (2013.01); *A61B 3/0016* (2013.01); *A61B 3/0075* (2013.01); *A61F 2/1613* (2013.01); *G02B 25/001* (2013.01)

(58) Field of Classification Search
CPC ...... A61B 3/032; A61B 3/0016; A61B 3/0075
(Continued)

(56) References Cited

U.S. PATENT DOCUMENTS 193,660 A * 7/1877 Kent ...................... A61B 3/032
                                                        351/239
698,833 A    4/1902 Hardy
(Continued)

FOREIGN PATENT DOCUMENTS

CN    202313272 U    7/2012
CN    104519784 A    4/2015
(Continued)

OTHER PUBLICATIONS

Office Action issued in Chinese Patent Application No. 201811117283.2 dated Jul. 9, 2021.
(Continued)

*Primary Examiner* — Zachary W Wilkes
(74) *Attorney, Agent, or Firm* — Nixon & Vanderhye (57) ABSTRACT

A vision measurement device includes an eyepiece with a lens; an outer tube connected to the eyepiece including a target having a predetermined pattern, the target being movable along an optical axis of the lens with respect to the outer tube; a diopter indicator with an indicating portion and a pointing portion; where during the movement of the target with respect to the outer tube along the optical axis of the lens, one of the indicator portion and the pointing portion moves along with the target with respect to the outer tube while the other of the indicator portion and the pointing portion does not move, and when an eye is capable of clearly
(Continued)

seeing the predetermined pattern on the target through the eyepiece, the value of the scale indicated by the pointing portion corresponds to the diopter of the eye.

17 Claims, 7 Drawing Sheets

(51) Int. Cl.
*A61F 2/16* (2006.01)
*G02B 25/00* (2006.01)

(58) Field of Classification Search
USPC .......................................... 351/239; 359/701
See application file for complete search history.

(56) References Cited

U.S. PATENT DOCUMENTS

| | | | |
|---|---|---|---|
| 783,125 A | | 2/1905 | Moore |
| 1,160,710 A | * | 11/1915 | Goodman .............. A61B 3/032 |
| | | | 351/239 |
| 1,174,547 A | * | 3/1916 | Clason .................. A61B 3/032 |
| | | | 351/237 |
| 1,684,555 A | * | 9/1928 | Ritholz ................... A61B 3/02 |
| | | | 351/239 |
| 3,669,529 A | * | 6/1972 | Guyton ............. G01M 11/0228 |
| | | | 351/239 |
| 5,455,645 A | * | 10/1995 | Berger ................... A61B 3/103 |
| | | | 351/223 |
| 5,557,352 A | * | 9/1996 | Nordquist ............ A61B 3/0008 |
| | | | 351/237 |
| 5,784,207 A | * | 7/1998 | Satoh ................... G02B 25/001 |
| | | | 359/700 |
| 9,215,977 B2 | * | 12/2015 | Kohn Bitran ........ A61B 3/0025 |
| 2007/0297070 A1 | * | 12/2007 | Shimizu ................... G02B 7/10 |
| | | | 359/701 |
| 2015/0164315 A1 | | 6/2015 | Drobe |
| 2015/0245764 A1 | * | 9/2015 | Guo ....................... A61B 3/032 |
| | | | 351/223 |
| 2016/0287070 A1 | | 10/2016 | Wang et al. |

FOREIGN PATENT DOCUMENTS

| | | |
|---|---|---|
| CN | 204293128 U | 4/2015 |
| CN | 105662329 A | 6/2016 |
| JP | S63-222736 A | 9/1988 |
| RU | 2137414 C1 | 9/1999 |

OTHER PUBLICATIONS

Extended European Search Report issued in European Patent Application No. 17306290.2 dated Jun. 18, 2018.
International Search Report and Written Opinion, dated Feb. 27, 2019, from corresponding PCT application No. PCT/EP2018/076053.

* cited by examiner

VISION MEASUREMENT DEVICE AND METHOD OF MEASURING VISION USING THE SAME

FIELD OF THE INVENTION

The present invention relates to vision measurement device and method of measuring vision of a measured eye with the vision measurement device.

BACKGROUND

Apparatus and methods for measuring the vision of human eye are known, and there have been developed various types of vision measurement devices implementing various kinds of principles. However, conventional apparatus for measuring refractive errors of the human eye contain large numbers of individual spherical and cylindrical lenses, and normally, conventional apparatus is large, cumbersome and expensive.

SUMMARY

The purpose of the invention is therefore to provide a solution to the defects in the prior art. i.e., to provide a simple and portable, low cost and easy to manufacture and use but robust device for vision measurement.

Embodiments of the present disclosure relates to an vision measurement device comprising: an eyepiece, in which a lens is provided and a distance from the lens to a viewing port of the eyepiece depends on a focal length of the lens; an outer tube connected to the eyepiece and in which a target having a predetermined pattern is provide, wherein the target is movable along an optical axis of the lens with respect to the outer tube; an indicating means for indicating diopter comprising an indicating portion and a pointing portion for indicating a diopter, wherein the indicator portion having a scale representing the diopter and the pointing portion indicating a value of the scale; wherein during the movement of the target with respect to the outer tube along the optical axis of the lens, one of the indicator portion and the pointing portion moves along with the target with respect to the outer tube while the other of the indicator portion and the pointing portion does not move, and when an eye is capable of clearly seeing the predetermined pattern on the target through the eyepiece, the value of the scale indicated by the pointing portion corresponds to the diopter of the eye.

Optionally, in the embodiments of the present disclosure, the predetermined pattern may include at least one of a diopter indicating portion located at a center thereof and an astigmatism indicating portion located at a periphery thereof.

Optionally, in the embodiments of the present disclosure, the vision measurement device may further comprise a blocking plate disposed between the viewing port and the target so as to block the diopter indicating portion and/or the astigmatism indicating portion when the target is observed by the eye.

Optionally, in the embodiments of the present disclosure, the vision measurement device may further comprise an engagement means configurable to prevent the target from moving in at least one of the directions along the optical axis of the lens.

Optionally, in the embodiments of the present disclosure, the vision measurement device may further comprise a restoring means configurable to restore the target to its initial position.

Optionally, in the embodiments of the present disclosure, the vision measurement device may further comprise: an inner tube provided in the outer tube; a guide on the outer tube and parallel to the optical axis of the lens, and a helical guide on the inner tube and extending about the optical axis of the lens, so that the inner tube and the outer tube are rotatable around the optical axis of the lens with respect to each other, to push the target to slide with respect to the guide and the helical guide and move along the optical axis of the lens; and an end cap on each of the inner tube and the outer tube at an end which is opposite to an end near the eyepiece.

Optionally, in the embodiments of the present disclosure, the vision measurement device may further comprise an engagement means configurable to prevent the target from moving in one of the directions along the optical axis of the lens. The engagement means may comprise a female ratchet located on the end cap of the outer tube, and a male ratchet connected to the end cap of the inner tube and rotating with the inner tube. Further, the male ratchet is capable of engaging with the female ratchet to prevent the inner tube and the outer tube from rotating with respect to each other in one direction, while allowing the inner tube and the outer tube to rotate with respect to each other in an opposite direction. In addition, the end cap of the inner tube is capable of being pulled outwards to disengage the male ratchet from the female ratchet such that the inner tube and the outer tube is capable of being rotated with respect to each other in both the one direction and the opposite direction.

Optionally, in the embodiments of the present disclosure, the vision measurement device may further comprise a restoring means configurable to restore the target to its initial position. The restoring means may comprise a torsion spring, one end of the torsion spring being fixed to the inner tube and the other end being fixed to the end cap of the outer tube, and the torsion spring may have restoring force only when the target leaves its initial position. Further, in the case that the target leaves its initial position, when the end cap of the inner tube is pulled outwards, the inner tube may rotate with respect to the outer tube due to the restoring force of the torsion spring, thereby moving the target back to its initial position.

Optionally, in the embodiments of the present disclosure, the initial position of the target may be located at the focal point of the lens, at an end of the inner tube near the eyepiece, or at an end of the inner tube which is opposite to the end near the eyepiece.

Optionally, in the embodiments of the present disclosure, the indicator portion may be located on an outer periphery of one of the end cap of the inner tube and the end cap of the outer tube, and the pointing portion may be located on an outer periphery of the other one of the end cap of the inner tube and the end cap of the outer tube.

Optionally, in the embodiments of the present disclosure, one of the end cap of the inner tube and the end cap of the outer tube may cover the other one of the end cap of the inner tube and the end cap of the outer tube, and the pointing portion may be located on the outer periphery of said one of the end cap of the inner tube and the end cap of the outer tube and may be a window through which the scale of the indicating portion on the outer periphery of said other one of the end cap of the inner tube and the end cap of the outer tube is exposed and the value of the scale is indicated.

Optionally, in the embodiments of the present disclosure, the indicating portion may be located on the outer tube and extend in parallel with the optical axis of the lens, and the pointing portion may be connected to the target and extend to the outside of the outer tube, so as to indicate the value of the scale. Optionally, in the embodiments of the present disclosure, the indicating portion may be located within the outer tube, extend in parallel with the optical axis of the lens and move along with the target, and the pointing portion may comprise a window located on the outer tube and through which the scale of the indicating portion is exposed and the value of the scale is indicated.

Optionally, in the embodiments of the present disclosure, the predetermined pattern on the target is interchangeable.

Optionally, in the embodiments of the present disclosure, at least one of the outer tube and the inner tube may be made of transparent or translucent material. Optionally, in the embodiments of the present disclosure, at least one of the outer tube and the inner tube may have through hole through which light from outside passes to illuminate the predetermined pattern on the target.

Optionally, in the embodiments of the present disclosure, the distance from the lens to the viewing port of the eyepiece may be configured such that when the eye views the predetermined pattern on the target while abutting on the viewing port of the eyepiece, reference position of the eye is positioned at the focal point of the lens.

Optionally, in the embodiments of the present disclosure, the reference position of the eye may comprise at least one of an anterior focal plane, a nodal point, and an entrance pupil of the eye.

Optionally, in the embodiments of the present disclosure, the distance from the lens to the viewing port of the eyepiece may be equal to a focal length of the lens.

According to another preferred embodiment of the invention, the target is movable along the optical axis of the lens inside the outer tube by means of a mechanism involving:
 a threaded cylindrical rod placed inside the outer tube and on which the target is mounted in rotation,
 a pinion gear interacting with said rod so that a rotation of said pinion gear leads to the rotation of said rod about its revolution axis,
 a notched ring that interacts with the pinion gear by meshing, so that a rotation of said ring leads to the rotation of said pinion gear thus leading to the rotation of the rod,
 a locking means preventing the target to rotate relative to the rod and allowing said target to slide along said rod by keeping the same spatial orientation.

The principle of this measurement device is to implement a mechanism intended to move the target along the rod inside the outer tube, which lies on an interaction between a pinion gear and a notched ring. A user wishing to know how is his sight, catch the measurement device and place his eye in front of the eyepiece in order to observe the target. If the image of the target appears to be blurry, he then adjusts the position of the target along the rod, in order to obtain a clear image of the target. To obtain such a result, he rotates the notched ring, preferably with his hand, in order to rotates the rod via the pinion gear, and since the target is locked in rotation relative to said rod, said target can only slide along the rod to get closer or away from his eye, by keeping the same spatial orientation. Once the user views a clear image of the target, the target is no more moved, and he can know the diopter corresponding to his eye, by looking at the pointing portion. Indeed, the pointing portion is simultaneously moved with the target, and when the target stops moving said pointing portion also stops moving in the same time to indicate a diopter value along a scale inscribed on the measurement device, advantageously on the outer tube of said device. Thus, a user can directly read the diopter value on the measurement device. With such a mechanism, a user can easily and with accuracy, move the target inside the measurement device without providing any effort. The target can directly be mounted in rotation on the rod, or can be mounted on said road with a support.

According to a possible characteristic, the mechanism is designed so that a rotation of the ring in one direction leads to a movement of the target in one direction along the rod, and a rotation of said ring in the other direction leads to a movement of the target in an opposite direction along said rod. This movement reversibility is made possible thanks to the interaction by meshing between the pinion gear and the notched ring. In function of his need, a user can easily move closer or farther the target from his eye with a simple rotation movement of the notched ring, without having to remove the measurement device from his eye.

According to a possible characteristic, the notched ring comprises an external surface on which some reliefs have been made so as to allow a manual rotation of said ring, the notched ring comprising an internal surface having notches intended to interact with the pinion gear. These reliefs aim to provide a rugosity on the notched ring to facilitate a manual rotation of said ring by a user. The reliefs can be for example made of protrusions and/or grooves.

According to a possible characteristic, the reliefs consist in a series of ribs regularly spaced around the ring. This kind of relief is easy to achieve and their machining is well controlled. Such a relief prevent the fingers of a user to slide on the ring making hard the ring handling by the user.

According to a possible characteristic, the outer tube comprises an internal channel having a specific cross section, and the locking means preventing the target to rotate relative to the rod is constituted by said internal channel which will serve as a guide for said target along the rod. Because of the specific geometry and the size of the cross section of the internal channel, the target cannot rotate about the rod. Since the rod rotates, the sole possible movement for the target is to slide along said rod by keeping the same spatial orientation.

According to a possible characteristic, the target is fixed to a support which is mounted in rotation on the rod and the target is bonded to the support with an adhesive material.

According to a possible characteristic, the target is circular shaped and comprises patterns that can be easily visually identifiable. Preferably, the patterns consist of different dark lines placed on a light background.

According to a possible characteristic, the patterns comprise a central circle and a plurality of radial lines connecting an external edge of the target to the central circle. Such a target is an illustrative example particularly suitable in the framework of a measurement device pursuant to the invention, but which is not limitative.

According to a possible characteristic, the position of the target along the rod is locked by means of an interaction between a ratchet spring solidarized to the notched ring and a fixed ratchet holder. Indeed, once the user has a clear image of the target, it is important to maintain said target in the position corresponding to this clear image, so as to allow the user to read quietly the diopter value on the measurement device. In this way, the locking device is systematically activated without any action of the user on the measurement device. Anywhere the target is placed along the rod, it is systematically locked in its position. The spring is flexible and advantageously comprises a tooth. The ratchet holder comprises a series of notches and the tooth is in contact with said notches. Due to the flexibility of the spring, when the ring rotates, the tooth can slide along said notches. But when the ring stops rotating, the tooth is naturally inserted in the corresponding notch facing said tooth, due to the spring relaxation.

According to a possible characteristic, the measurement device comprises an eyepiece cap articulated mounted on the eyepiece between a closing position for which it closes an orifice of said eyepiece through which a user will look at the target, and an opening position for which it has rotated with an angle greater than 90° to release said orifice. In this way, the eyepiece cap is always linked to the measurement device without any possibility to lose said cap. In the closing position the cap protects the orifice and the measurement device is in an inactive configuration. If a user wishes to use the measurement device, he makes rotate the eyepiece cap with an angular amplitude of at least 90° before placing his eye in front of the orifice. Advantageously the angular amplitude is 180° more or less 20°.

According to a possible characteristic, the eyepiece cap comprises an arm and an enlarged head, said eyepiece being articulated at the level of said arm and the enlarged head being intended to close the orifice of the eyepiece. In this way, the enlarged head is not directly involved in the eyepiece cap rotation and thus can serve efficiently to close the orifice. For this configuration, the cap is comparable to a spoon.

According to a possible characteristic, the measurement device is made of plastic material. This material is light compared to a metal, and has a good mechanical strength. This material may be for example transparent to allow the target to be continuously lighted by the light of day.

According to a possible characteristic, the indicator portion has a scale representing the diopter and which extends outside and along the outer tube parallelly to the rod, the pointing portion being a cursor which moves along the scale simultaneously with the target. It is advantageously supposed that the cursor is situated outside the outer tube so that a user can directly read the diopter value indicated by said cursor. Preferably, the cursor is solidarized to the target and moves simultaneously with said target.

Another aspect of the embodiments of the present disclosure relates to a method of measuring vision of a measured eye with the vision measurement device of the present disclosure, comprising: moving the target while the measured eye viewing the predetermined pattern on the target through the eyepiece until the measured eye is capable of clearly seeing the predetermined pattern, and recording the value of scale of the indicator portion indicated by the pointing portion.

BRIEF DESCRIPTION OF THE DRAWINGS

In order to more clearly describe the technical solutions in the embodiments of the present invention or in the prior art, the accompanying drawings that need to be used in the embodiments or in the prior art are briefly introduced. Obviously, these accompanying drawings are merely some embodiments of the present invention, and for one of ordinary skill in the art, other drawings can be obtained based on these accompanying drawings without paying any creative efforts.

DESCRIPTION OF THE EMBODIMENTS

Figure 1:
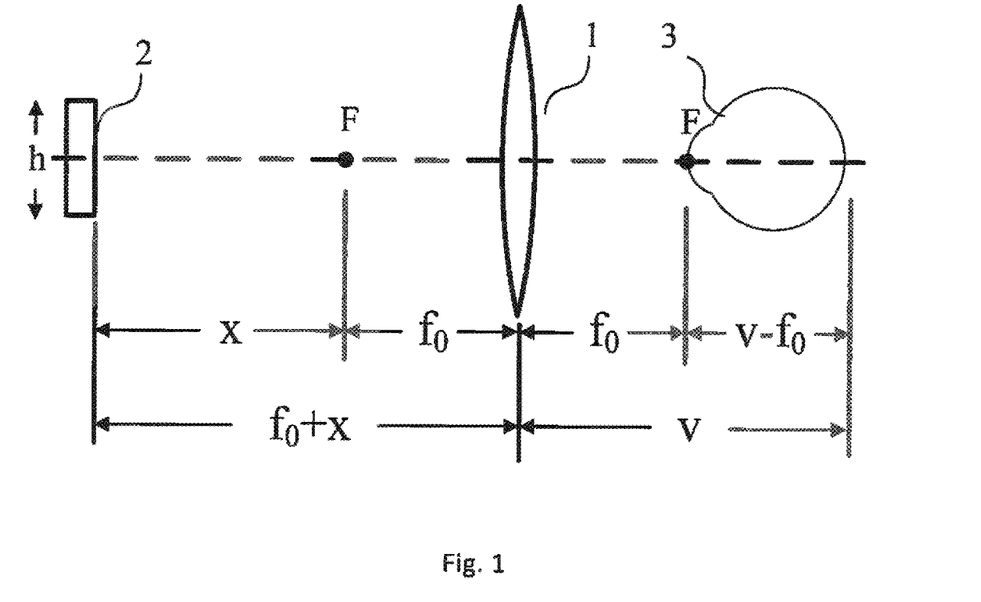
FIG. 1 is a schematic representation of the optical principle of the vision measurement device according to the embodiments of the present disclosure.

FIG. 1 is a schematic representation of the optical principle of the vision measurement device according to the embodiments of the present disclosure.

In FIG. 1, a lens 1 is provided. In some embodiments of the present disclosure, the lens is not limited to a singular lens, and can also be a combination of a plurality of lenses. A target 2 is located on the optical axis of the lens at the anterior side of the lens and is movable along the optical axis of the lens. A human eye 3 is located on the optical axis of the lens at the posterior side of the lens. Throughout the present disclosure, the term "anterior" and "posterior" is determined with reference to the position of the eye when using the vision measurement device: the side which is nearer to the eye is referred to as the posterior side and the side which is farther from the eye is referred to as the anterior side. The reference position of the eye is located at the posterior focal point of the lens. The reference position of the eye comprises at least one of the anterior focal plane, the nodal point, and the entrance pupil of the eye. The focal length of the lens is $f_0$. The distance between the anterior focal point of the lens and the target is represented by x, and thus the object distance is $(f_0+x)$. Based on the optical structure of human eye, when the eye 3 can clearly see the target 2, the target 2 is imaged on the retina of the eye 3 and the image distance is represented by v.

Based on the Gaussian equation, the optical system shown in FIG. 1 can be expressed as:

$$\frac{1}{v} + \frac{1}{f_0 + x} = \frac{1}{f_0} \quad (1)$$

In addition, the diopter D of the eye is expressed as:

$$\frac{1}{v - f_0} = D \text{ or } f_0 + \frac{1}{D} = v \quad (2)$$

By substituting equation (2) into the parameter v in equation (1), equation (1) becomes:

$$\frac{1}{f_0 + x} + \frac{1}{f_0 + \frac{1}{D}} = \frac{1}{f_0} \quad (3)$$

By solving equation (3), it can be determined that $$D = \frac{x}{f_0^2} \quad (4)$$

Based on equation (4), it can be seen that the diopter D of the eye is in linear relationship with the distance between the target and the anterior focal point of the lens. With this configuration, the scale for indicating the diopter D of the eye is also linearly related to the axial displacement of the target, and thus a linear scale in diopters may be constructed. Also, it would be much easier to read the value of the scale when measuring the diopter of the measured eye.

In addition, the angular size of the target image con the retina is expresses as:

$$\theta = \frac{h}{f_0} \quad (5)$$

wherein h is the height of the target 2.

Based on equation (5), it can be seen that the angular size of the target image is independent from the position of the target, and thus the size of the target image is constant while varying the position of the target. With this configuration, since the size of the target image is constant, during the measurement of the diopter D of the measured eye, the measured eye will not be stimulated by the change of the size of the target image to accommodate.

Figure 2:
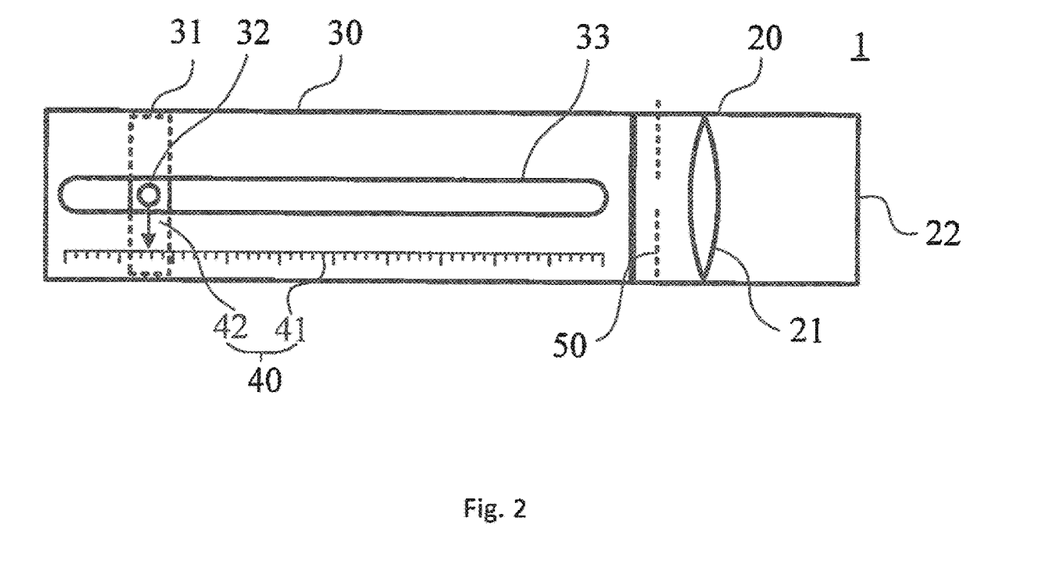
FIG. 2 is a schematic representation of the structure of the vision measurement device according to the embodiments of the present disclosure.

FIG. 2 is a schematic representation of the structure of the vision measurement device 1 according to the embodiments of the present disclosure.

As shown in FIG. 2, in the embodiments of the present disclosure, the vision measurement device 1 at least comprises an eyepiece 20, an outer tube 30, and an indicating means 40 for indicating diopter.

In the eyepiece 20, a lens 21 is provided and the optical axis of the lens 21 coincides with or at least is in parallel with the longitudinal axis of the eyepiece 20. A distance from the lens 21 to a viewing port 22 of the eyepiece 20 depends on a focal length $f_0$ of the lens 21. The viewing port 22 is on the posterior side of the lens 21 and forms the posterior end of the eyepiece 20. In some embodiments of the present disclosure, the distance is configured such that when the eye abuts on the viewing port 22 of the eyepiece 20, the reference position of the eye is positioned at the posterior focal point of the lens 21. The reference position of the eye comprises at least one of the anterior focal plane, the nodal point, and the entrance pupil of the eye. In some embodiments of the present disclosure, the distance from the lens to the viewing port of the eyepiece is equal to the focal length of the lens 21. In some embodiments of the present disclosure, the distance can be made smaller than those in the previous embodiments, such that the eye may view the target through the eyepiece 20 with a distance between the viewing port 22 and the eye, i.e., without abutting on the viewing port 22 of the eyepiece 20. In this case, for example, docketing accessories can be used to docket the eye to the viewing port 22 of the eyepiece 20 for hygiene or sterilization purpose.

The outer tube 30 is capable of being connected to the eyepiece 20 at the anterior end of the eyepiece 20 and the longitudinal axis of the outer tube 30 coincides with or at least is in parallel with the optical axis of the lens 21 and the longitudinal axis of the eyepiece 20. In the outer tube 30, a target 31 is provided. The target 31 is movable along an optical axis of the lens with respect to the outer tube. The movement range of the target 31 might be the as large as the total length of the outer tube 30, that is, between the anterior end of the outer tube 30 and the posterior end of the outer tube 30. In some embodiments of the present disclosure, the movement range of the target 31 can be smaller than the total length of the outer tube 30, as long as the anterior focal point of the lens 21 is located within the movement range of the target 31.

On the target 31, a protrusion 32 is provided, and on the outer tube 30, a guide 33 which is parallel to the optical axis of the lens 21 is provided. The protrusion 32 extends through the guide 33 and to the outside of the outer tube 30 such that the user can move the target 31 by pushing the protrusion 32. In FIG. 2, only one guide 33 and one protrusion 32 are shown. In some embodiments of the present disclosure, there could be another guide 33 and another protrusion 32 on the other side of the device. The person skilled in the art can easily appreciate that any other structures that can be used to move the target 31 within the outer tube 30 are included in the present disclosure.

Figure 3:
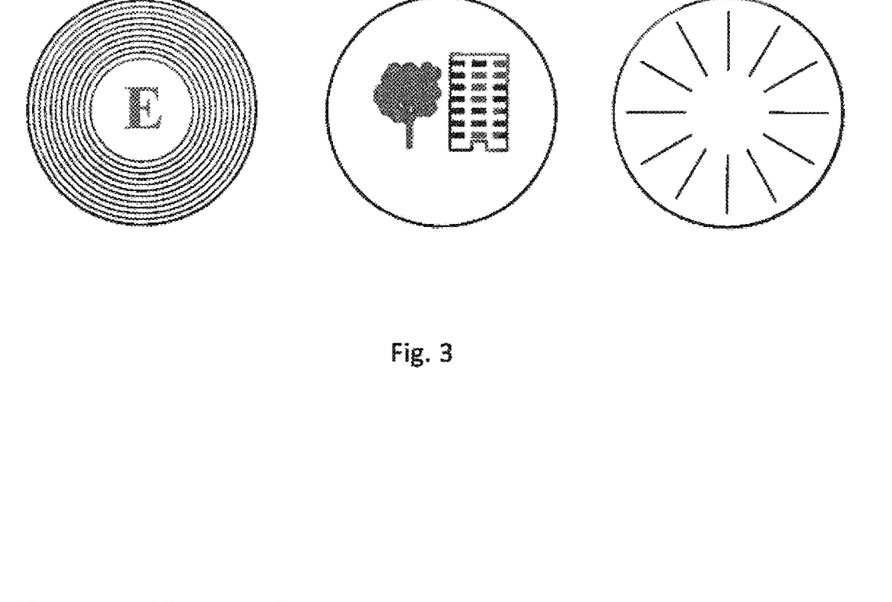
FIG. 3 shows some schematic representations of the predetermined pattern on the target according to the embodiments of the present disclosure.

On the posterior side of the target 31, i.e., the side facing the lens 21, at least one predetermined pattern is provided. The predetermined pattern includes at least one of a diopter indicating portion and an astigmatism indicating portion. FIG. 3 shows some schematic representations of the predetermined pattern on the target according to the embodiments of the present disclosure. As shown in FIG. 3, the predetermined pattern comprises the diopter indicating portion located at a center of the target 31, and the astigmatism indicating portion located at a periphery of the target 31. The diopter indicating portion comprises at least one of Latin letters, such as "E" or "C", icons, such as "tree and building" and other patterns known in this technical filed. The astigmatism indicating portion comprises at least one of concentric rings or radial lines. The person skilled in the art would easily appreciate that any patterns used in the technical field of vision measurement can be included in the present disclosure. In some embodiments of the present disclosure, the predetermined pattern includes only one of the diopter indicating portion and the astigmatism indicating portion, and the predetermined pattern is interchangeable between several patterns. For example, the outer tube 30 and the eyepiece 20 can be separated from each other and the pattern on the target 31 can be removed from the posterior end of the outer tube 30 and replaced with other patterns.

In some embodiment of the present disclosure, a blocking plate 50 can be disposed between the viewing port 22 and the target 31 so as to block one of the diopter indicating portion and the astigmatism indicating portion when the target is observed by the measured eye. For example, as shown in FIG. 2, the blocking plate 50, which has a through hole at its center, is adjacent to the lens 21 on the anterior side thereof, and when the target is observed by the measured eye, the astigmatism indicating portion is blocked by the blocking plate 50 such that the user will not be distracted by astigmatism indicating portion. Alternatively, the blocking plate 50 can block the diopter indicating portion, such that the user will not be distracted by diopter indicating portion. In some embodiments of the present disclosure, the blocking plate 50 can be located on the posterior side of the lens 21, or any other place within the vision measuring device 1, as long as it can block one of the diopter indicating portion and the astigmatism indicating portion when the target is observed by the measured eye.

An indicating means 40 for indicating diopter is provided on the outer tube 30 to indicate diopter of the measured eye. The indicating means 40 comprises an indicating portion 41 and a pointing portion 42 for indicating the value of the diopter. In some embodiments of the present disclosure, the indicator portion 41 has a scale representing the diopter, and as had discussed above, the scale in diopters is linearly related to the axial displacement of the target 31. In some embodiments, one of the indicator portion 41 and the pointing portion 42 moves along with the target 31 with respect to the outer tube 30, and the other one does not move, such that the relative movement of the indicator portion 41 and the pointing portion 42 represents the movement of the target 31 with respect to the outer tube 30. As shown in FIG. 2, the indicator portion 41 is located on the outer tube 30, for example, on the outer surface of the outer tube 30 and the scale extends along the longitudinal direction of the outer tube 30. Further, the pointing portion 42 is connected to the target 31 and moves along with the target 31. In these embodiments, the pointing portion 42 might be an arrow pointing at the value of the scale. In some other embodiments of the present disclosure, the indicator portion 41 is coupled to the target 31 and moves along with the target 31, and the scale extends along the longitudinal direction of the outer tube 30. The indicator portion 41 may be located within the outer tube 30. Further, the pointing portion 42 may be located on the outer tube 30, for example, on the outer surface of the outer tube 30. In these embodiments, the pointing portion 42 might be a window through which the scale of the indicating portion 41 is exposed and the value of the scale is indicated. Other embodiments of the indicator portion 41 and the pointing portion 42 are provided in the following parts of the present disclosure.

As to the scale of the indicator portion 41, each value of the scale indicated by the pointing portion 42 corresponds to the diopter of the eye when such eye is capable of clearly seeing the predetermined pattern on the target through the eyepiece. In terms of the optical structure of human eye, when the eye can clearly see the pattern, the pattern is imaged on the retina of the eye. In addition, in the embodiments of the present application, whether a user can "clearly see" the pattern on the target 31 can be determined subjectively by the user. Generally speaking, a human eye in the state of emmetropia can "clearly see" the object located from its near point to infinity, and thus when the user with the measured eye can see the pattern as if the measured eye is in the case of emmetropia, the measured eye can "clearly see" the pattern. Also, the values of the scale can be determined through the above equation (4) by establishing the relationship between the displacement of the target 31 from the anterior focal point of the lens 21 and the relative positions of the pointing portion 42 on the scale of the indicator portion 41. In some embodiments of the present disclosure, when the target 31 is located at the anterior focal point of the lens 21, a human eye in the state of emmetropia can "clearly see" the target 31, and thus value of the diopter indicated by the point 42 is zero.

Below, an example for the process of measuring the vision of eye with the vision measurement device according to the embodiments of the present disclosure is described.

The vision measurement device 1 can be held by the hand of the user or supported by a stand. Then, the user places the measured eye at the viewing port 22 of the eyepiece 20 and views the predetermined pattern on the target 31 through the lens 21 with the measured eye. Due to the position of the target 31 and the diopter of the eye, the user may not clearly see the predetermined pattern on the target 31. Thereafter, the user moves the target 31 along the optical axis of the lens 21 until the user can clearly see the target 31 with the measured eye. At this time, the value of the scale indicated by the pointing portion 42 corresponds to the diopter of the measured eye. The diopter thus determined can be used to prescribe the lens for the measured eye. As noted above, the clearness of the target viewed with the measured eye is subjectively determined by the user. In some embodiments of the present disclosure, the person skilled in the art can appreciate several ways for modifying the diopter thus determined so as to obtain a more accurate diopter for the measured eye.

The vision measurement device 1 according to the embodiments of the present disclosure can also be used to determine the astigmatism of the measured eye.

When the user can clearly see the target 31 at a first position with the measured eye, if he/she detects blur of the astigmatism indicating portion in one direction which is in parallel with the surface of the predetermined pattern and/or see more clearly in one direction which is in parallel with the surface of the predetermined pattern, it can be determined that the measured eye suffers from astigmatism, and the direction represents the cylinder axis of the measured eye. Then, the user has to find a second position of the target 31 at which the user can detects blur of the astigmatism indicating portion in one direction and/or see more clearly in one direction. The difference between the diopters determined at the first position and the second position represents the astigmatism of the user. The direction in which the user can detect blur when the target 31 is located at the first position is perpendicular to the direction in which the user can detect blur when the target 31 is located at the second position.

In the above process, as an initial position, the target 31 can be located at the posterior end of the outer tube 30, which is near the measured eye and within the near point of the measured eye. By starting the movement of the target 31 from the position within the near point of the measured eye, when the user can clearly see the target for the first time, the target 31 is located at the near point of the measured eye, and the diopter thus determined is more accurate to prescribe the lens for the measured eye.

In addition, in some embodiments of the present disclosure, the initial position of the target 31 can be any other place within its movement range, for example, at the anterior end of the outer tube 30, at the anterior focal point of the lens 21, and the diopter thus determined is still accurate enough to prescribe the lens for the measured eye. When the initial position of the target 31 is at the anterior focal point of the lens 21, it is possible to measure the diopter in the positive direction and in the negative direction with less movement of the target and thus reduce the time consumed when the vision measurement device the present disclosure is used to measure the visions of people including the patients suffering from myopia and the patients suffering from hyperopia.

In some embodiments of the present application, an engagement means (not shown in FIG. 2) can be provided to the vision measurement device 1. The engagement means is configurable to prevent the target from moving in at least one of the directions along the optical axis of the lens. In some embodiments of the present application, when the measured eye can clearly see the predetermined pattern on the target, the engagement means can be activated such that the target is not movable in both directions along the optical axis of the lens. With such configuration, it is more convenient to read the value of the scale by the user himself or handing the vision measurement device 1 over to someone else, such as the optician.

In some embodiments of the present application, while the target moves in one direction, the engagement means can prevent the target from moving backward. That is to say, the engagement means is configurable to ensure that the target travels only in one direction. With such configuration, it is possible to prevent the target from backing into the area of accommodation of the eye and thereby reaching the far point of the eye or somewhere between the far point and the near point of the eye. When the target is at the far point of the eye or somewhere between the far point and the near point of the eye, the user can still clearly see the predetermined pattern on the target and thus gives the wrong value for the diopter of the eye. In addition, once the user can clearly see the predetermined pattern on the target at the near point and then bring the target back towards his eye, it is possible that the user can still focus on it, and thus gives the wrong value for the diopter of the eye. With this configuration, it is possible to avoid this situation either.

The person skilled in the art can appreciated that any structure known in the technical filed of mechanics that can restrict the movement of target and/or fasten the target can be used in the vision measurement device of the present disclosure as the engagement means, such as those implementing gears, racks, worm wheels, chains, screws, snaps and so on. Other embodiments relating to the detailed structure of the engagement means are provided in the following parts of the present disclosure.

In some embodiments of the present application, a restoring means (not shown in FIG. 2) can be provided to the vision measurement device 1. The restoring means is configurable to restore the target to its initial position. For example, in some embodiments of the present disclosure, the restoring means can be a spring disposed in the outer casing 1 and connected between the target and one end of the outer tube and generates restoring force once the target leaves its initial position. Thus, when the measurement is finished or the user releases the target, the target will be push or pull back to its initial position. With this configuration, it is possible to restore the target to its initial position once the measurement is finished and thus release the user from duplication of effort.

The person skilled in the art can appreciated that any structure known in the technical filed of mechanics that can accumulating energy when the target moves and restore the target to its initial position once the target is released can be used in the vision measurement device of the present disclosure as the restoring means, such as those implementing springs, coil springs, leaf springs, and so on. Other embodiments relating to the detailed structure of the restoring means are provided in the following parts of the present disclosure.

In some embodiments of the present application, the engagement means and the restoring means can be incorporated into the same vision measurement device. In these embodiments, when the target leaves its initial position, the restoring means generates restoring force for restoring the target to its initial position. However, because of the engagement means, the target is prevented from moving backwards to its initial position. Then, when the engagement means is deactivated, it does not restrict the movement of target any longer, and due to the restoring force of the restoring means, the target moves back to its initial position. With this confirmation, it is possible to implement both the engagement means and the restoring means in a simple and compact structure, and thus the size and the cost of the vision measurement device as well as the complexity for manipulating the vision measurement device can be reduced.

Below, some embodiments of the vision measurement device 2 according to the embodiments of the present disclosure will be described with reference to FIG. 4.

Figure 4:
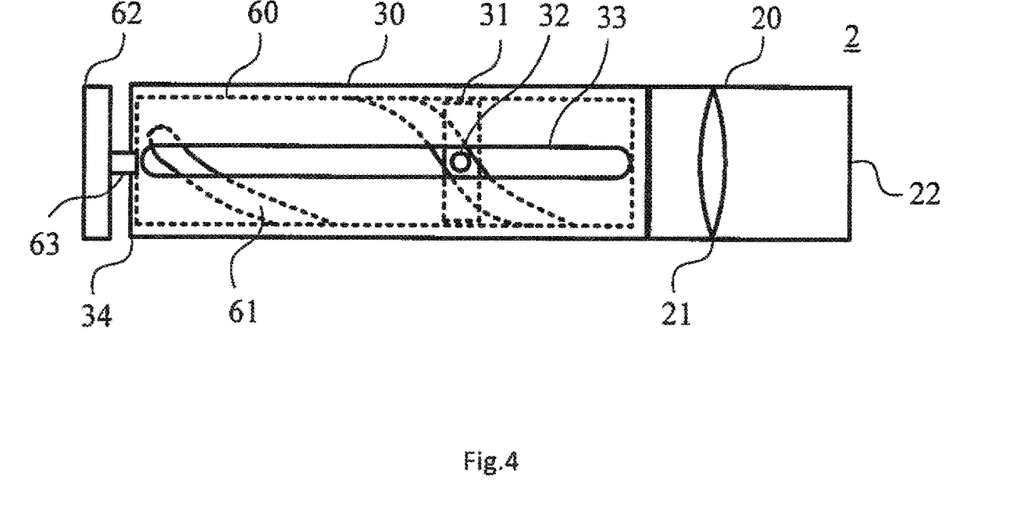
FIG. 4 is a schematic representation of the structure of the vision measurement device according to the embodiments of the present disclosure.

As shown in FIG. 4, in the vision measurement device 2, an inner tube 60 is further provided in the outer tube 30 and the target 31 is located within the inner tube 60. The inner tube 60 and the outer tube 30 are rotatable around the optical axis of the lens 21 with respect to each other. Further, similar to FIG. 2, on the outer tube 30, a guide 33 which is parallel to the optical axis of the lens 21 is provided. In addition, on the inner tube 60, a helical guide 61 extending about the optical axis of the lens is provided. The target 31 can slide along the guide 33 and the helical guide 61 and thus when the inner tube 60 and the outer tube 30 rotate with respect to each other, the target 31 is pushed by the guide 33 and 61 so as to move along the optical axis of the lens.

On the anterior end, i.e., an end which is opposite to an end near the eyepiece 20, the inner tube 60 and outer tube 30 are provided with end cap 62 and 34, respectively. The end cap 62 of the inner tube 60 is on the anterior side of the end cap 34 of the outer tube 30 and is connected to the inner tube 60 via a connection shaft 63 through the end cap 34 of the outer tube 30. Then, the user can rotate the inner tube 60 by rotating the end cap 62 thereof.

In FIG. 4, similar to FIG. 2, only one helical guide 61 is shown. In some embodiments of the present disclosure, there could be another helical guide 61 on the other side of the device, and thus the helical guide 61 has the shape of double helix.

In the vision measurement device 2 shown in FIG. 4, by rotating the end cap 62 of the outer tube 60, it is possible to move the target 31 in a more accurate and efficient way as compared to the vision measurement device 1 shown in FIG. 2.

In some embodiments of the present invention, the vision measurement device 2 may adopt the indicating means 40 shown in FIG. 2 as well. In some other embodiments of the present invention, as shown in FIG. 5, the vision measurement device 2 is provided with an indicating means 40 located on the end cap 62 and 34.

Figure 5:
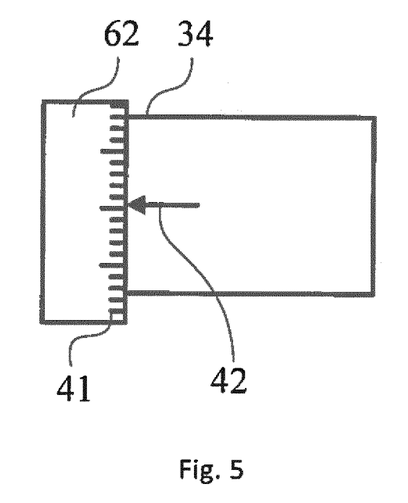
FIG. 5 is an enlarged view showing a schematic representation of the indicating means of the vision measurement device according to the embodiments of the present disclosure.

FIG. 5 is an enlarged view showing a schematic representation of the indicating means of the vision measurement device according to the embodiments of the present disclosure. As shown in FIG. 5, the indicator portion 41 is located on an outer periphery of the end cap 62 of the inner tube 60 and the pointing portion 42 is located on an outer periphery of the end cap 34 of the outer tube 30. Alternatively, in some other embodiments of the present disclosure, the indicator portion 41 is located on an outer periphery of the end cap 34 of the outer tube 30 and the pointing portion 42 is located on an outer periphery of the end cap 62 of the inner tube 60. By rotating the inner tube 60 and the outer tube 30 with respect to each other, displacement between the indicator portion 41 and the pointing portion 42 corresponds to the displacement of the target 31 along the optical axis of the lens 21, and thus the value of the scale indicated by the pointing portion 42 corresponds to the diopter of the measured eye. In some embodiments of the present disclosure, the outer periphery of the end cap 34 might cover at least a portion of the outer periphery of the end cap 62, and then the pointing portion 42 is located on the outer periphery of the end cap 34 and is a window through which the scale of the indicating portion 41 on the outer periphery of the end cap 62 is exposed and the value of the scale is indicated. Alternatively, in some other embodiments of the present disclosure, the outer periphery of the end cap 62 might cover at least a portion of the outer periphery of the end cap 34, and then the pointing portion 42 is located on the outer periphery of the end cap 62 and is a window through which the scale of the indicating portion 41 on the outer periphery of the end cap 34 is exposed and the value of the scale is indicated.

In the vision measurement device 2 shown in FIG. 4, in addition to the engagement means discussed with reference to FIG. 2, an engagement means comprising a female ratchet and a male ratchet can be provided to the end cap 62 of the inner tube 60 and the end cap 34 of the outer tube 30.

Figure 6:
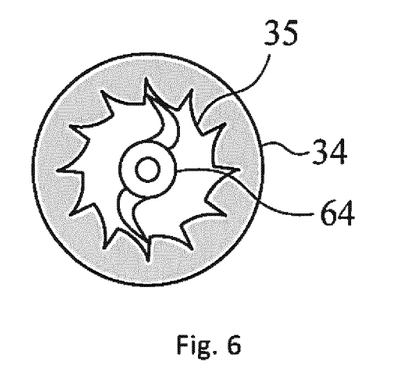
FIG. 6 is a side view of the engagement means from the anterior side of the vision measurement device of the present disclosure, in which the end cap of the inner tube is omitted.

FIG. 6 is a side view of the engagement means from the anterior side of the vision measurement device of the present disclosure, in which the end cap 62 of the inner tube 60 is omitted. In FIG. 6, it can be seen that a female ratchet 35 is located on the end cap 34 of the outer tube 30, and a male ratchet 64 is provide such that it is connected to the end cap 62 of the inner tube 60 and rotates with the inner tube 60. As shown in FIG. 6, the male ratchet 64 is capable of engaging with the female ratchet 35 such that the inner tube 60 and the outer tube 30 is prevented from rotating with respect to each other in one direction (counter-clockwise direction), while being allowed to rotate with respect to each other in an opposite direction (clockwise direction). Further, the end cap 62 of the inner tube 60 is capable of being pulled outwards along with the male ratchet 64 to disengage the male ratchet 64 from the female ratchet 35 such that the inner tube 60 and the outer tube 30 is capable of being rotated with respect to each other in both directions.

The engagement means shown in FIG. 6 is simple and compact, and thus the size and the cost of the vision measurement device, as well as the complexity for manipulating the vision measurement device can be reduced.

Further, for the vision measurement device, the restoring means can be provided to the end cap 62 of the inner tube 60 and the end cap 34 of the outer tube 30 as well.

Figure 7:
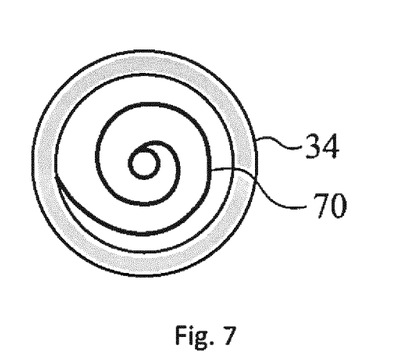
FIG. 7 is a side view of the restoring means from the anterior side of the vision measurement device of the present disclosure, in which the end cap of the inner tube is omitted.

FIG. 7 is a side view of the restoring means from the anterior side of the vision measurement device of the present disclosure, in which the end cap 62 of the inner tube 60 is omitted. In the embodiments shown in FIG. 7, the restoring means comprises a torsion spring 70, which is coaxially disposed with respect to the end cap 62 of the inner tube 60 (omitted in FIG. 7) and the end cap 34 of the outer tube 30. The end of the torsion spring 70 at the center thereof is fixed to inner tube 60 by, for example, fastening to the connection shaft 63, and the outermost end of the torsion spring 70 is fixed to the end cap 34 of the outer tube 30. Thus, when the inner tube 60 and the outer tube 30 rotates with respect to each other, the target 31 leaves its initial position, and the torsion spring generates restoring force for restoring the target 31 to its initial position. When the end cap 62 of the inner tube 60 is released by the user, due to the restoring force of the torsion spring 70, the inner tube 60 rotates backwards with respect to the outer tube 30, thereby moving the target 31 back to its initial position.

With this confirmation, it is possible to implement the restoring means in a simple and compact structure, and thus the size and the cost of the vision measurement device, as well as the complexity for manipulating the vision measurement device can be reduced.

Figure 8:
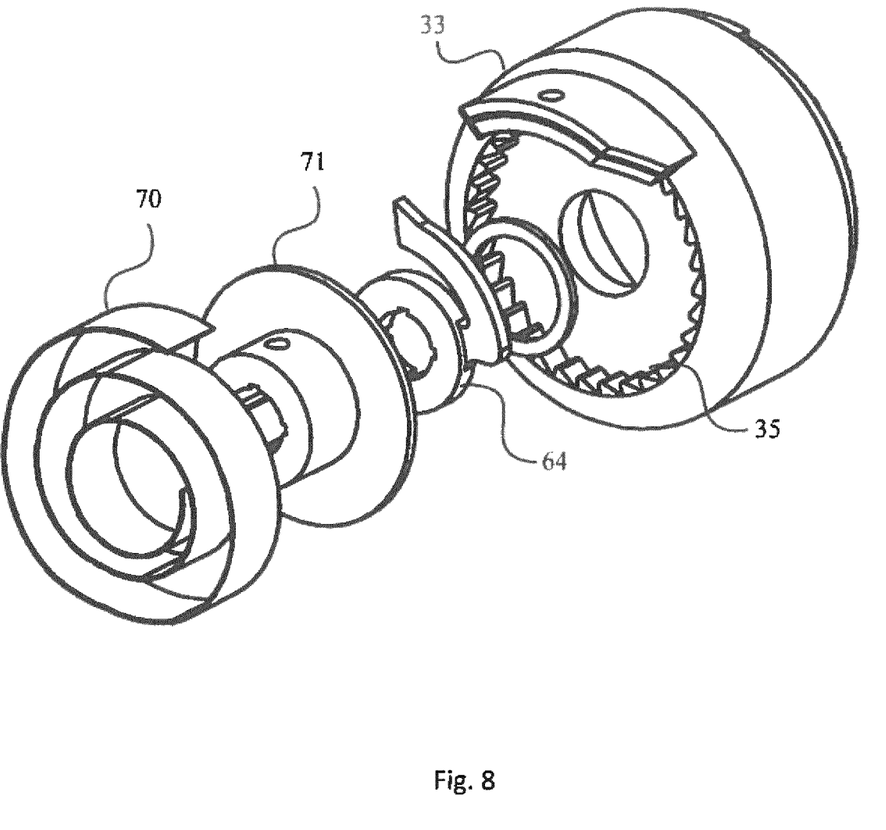
FIG. 8 is a perspective view of the engagement means and restoring means from the anterior side of the vision measurement device of the present disclosure, in which the end cap of the inner tube is omitted.

In some embodiment of the present disclosure, the engagement means shown in FIG. 6 and the restoring means shown in FIG. 7 can be incorporated into the same vision measurement device. FIG. 8 is a perspective view of the engagement means and restoring means from the anterior side of the vision measurement device of the present disclosure, in which the end cap 62 of the inner tube 60 is omitted.

As shown in FIG. 8, the torsion spring 70 and the male ratchet 64 are coaxially disposed with respect to the end cap 62 of the inner tube 60 (omitted in FIG. 8) and the end cap 34 of the outer tube 30. Similar to FIG. 6, the male ratchet 64 is capable of engaging with the female ratchet 35 such that the inner tube 60 and the outer tube 30 is prevented from rotating with respect to each other in one direction (counter-clockwise direction), while being allowed to rotate with respect to each other in an opposite direction (clockwise direction). The end of the torsion spring 70 at the center thereof is fixed to inner tube 60 by, for example, fastening to spring base 71, and the outermost end of the torsion spring 70 is fixed to the end cap 34 of the outer tube 30. The spring base 71 is mounted on the connection shaft 63 (omitted in FIG. 8) and rotates along with the end cap 62 of the inner tube 60. In addition, the spring base 71 also functions as a spacer separating the torsion spring 70 from the male ratchet 64. In these embodiments, when the inner tube 60 and the outer tube 30 rotate with respect to each other, the target 31 leaves its initial position, the torsion spring generates restoring force for restoring the target 31 to its initial position. However, because of the engagement of the female ratchet 35 and the male ratchet 64 of the engagement means, the inner tube 60 and the outer tube 30 are prevented from rotating backwards with respect to each other. Then, when the end cap 62 of the inner tube 60 is pulled outwards by the user along with the male ratchet 64, the engagement of the female ratchet 35 and the male ratchet 64 is released, and due to the restoring force of the torsion spring 70, the inner tube 60 rotates backwards with respect to the outer tube 30, thereby moving the target 31 back to its initial position.

With this confirmation, it is possible to implement both the engagement means and the restoring means in a simple and compact structure, and thus the size and the cost of the vision measurement device, as well as the complexity for manipulating the vision measurement device can be reduced.

In some embodiments, at least one of the outer tube 30 and the inner tube 60 is made of transparent or translucent material, such that the light from the outside of the vision measurement device can illuminate the predetermined pattern on the target. In some other embodiments, at least one of the outer tube 30 and the inner tube 60 has through holes through which light from outside passes to illuminate the predetermined pattern on the target. With these configurations, the cost of the vision measurement device can be reduced.

Figures 11, 12:
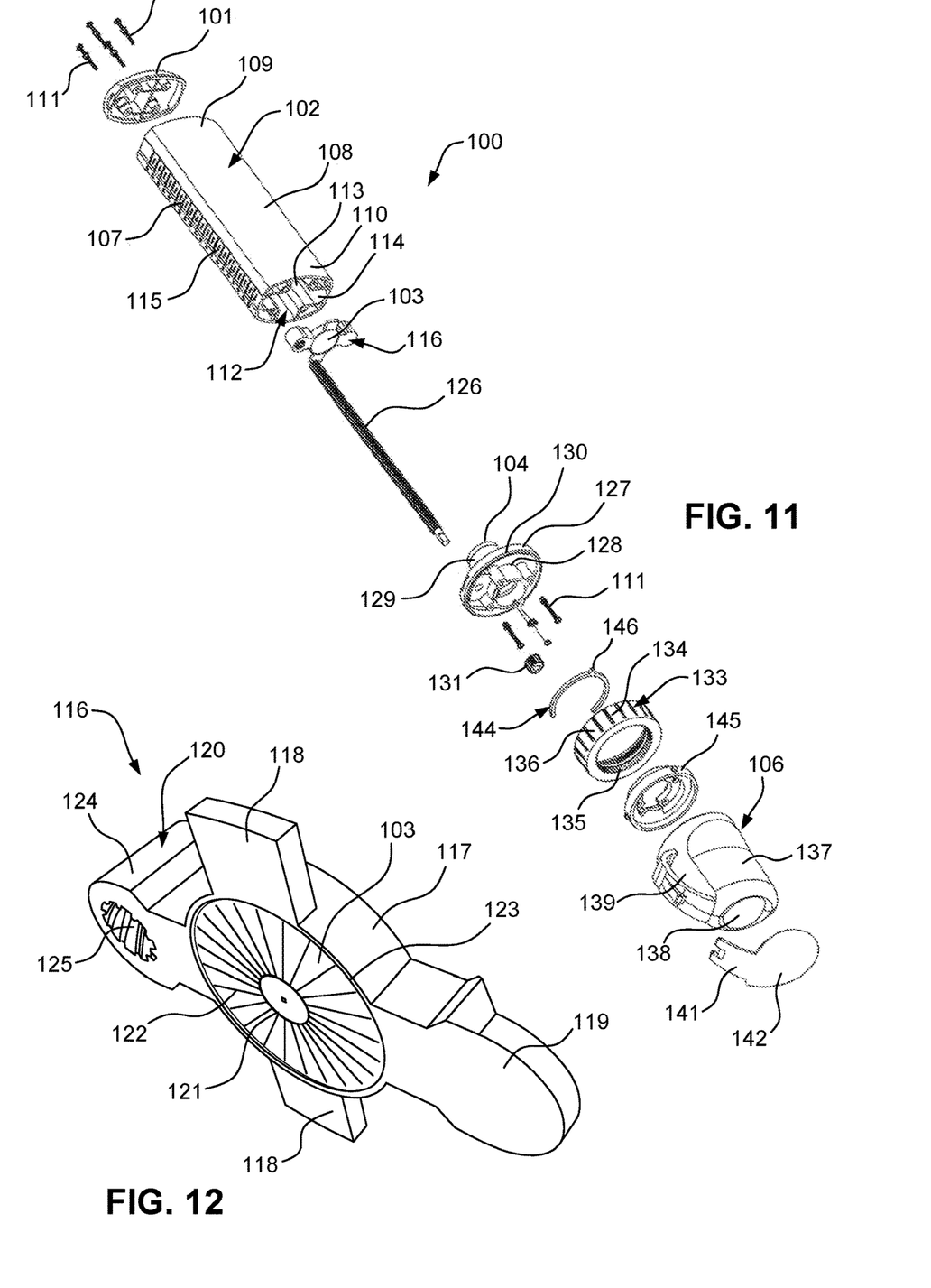
FIG. 11 is an exploded perspective view of the measurement device of FIG. 9A.
FIG. 12 is a perspective view of a target support of the measurement device of FIG. 9A.

Referring to FIG. 11, a preferred embodiment of a measurement device 100 pursuant to the invention schematically comprises an endcap 101, an outer tube 102, a target 103, a fixed lens 104, movement means of said target 103, and an eyepiece 106.

Referring to FIGS. 9A, 9B, 11 and 13 the outer tube 102 is substantially parallelepipedal, with an external cross section substantially rectangular. This external cross section is delimited by two parallel short sides 107 and by two parallel long sides 108, these four sides 107, 108 being slightly curved so as to avoid the presence of sharp edges on the outer tube 102. The outer tube 102 is elongated and presents a first extremity 109 and a second extremity 110 considered with respect to a longitudinal axis of said outer tube 102.

Referring to FIG. 11, the first extremity 109 of the outer tube 102 is closed by the endcap 101 which is fixed to said extremity 109 by means of screws 111. The endcap 101 is a slightly curved rectangular piece having a thin thickness, typically less than 3 mm, and which comes to fit on this first extremity 109. Preferably, the endcap 101 and the outer tube 102 are made with the same material The outer tube 102 comprises an internal channel 112 which extends along a longitudinal axis of said tube 102 and which has a cross-shaped cross section. This cross section presents a first short rectangular portion 113 and a second long rectangular portion 114, these two portions 113, 114 being perpendicular and intersecting in their middle. In other words, this cross section has two symmetric axes, one extending along the first portion 113 and being situated in the middle of said first portion 113, and the other extending along the second portion 114 and being situated in the middle of said second portion 114, In this way, the first rectangular portion 113 comprises two aligned short branches which are separated by the second long rectangular portion 114, and inversely, the second rectangular portion 114 comprises two aligned long branches which are separated by the first short rectangular portion 113.

Figure 13:
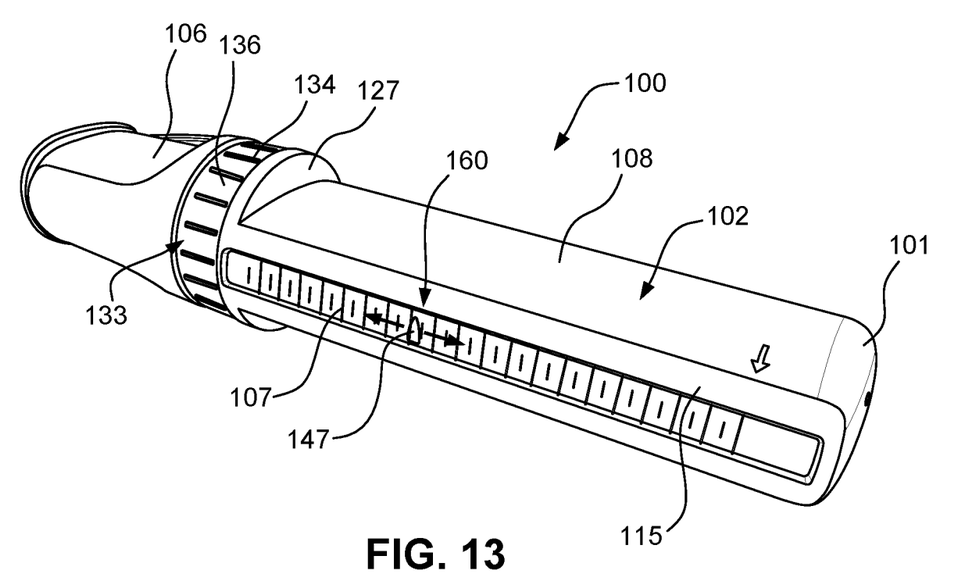
FIG. 13 is a perspective view of the measurement device of FIG. 9A, showing an indicating portion having a scale representing the diopter.

Referring to FIGS. 11 and 13, the outer tube 102 includes an indicating portion 115 in the form of a graduated scale extending along the outer tube 102. This scale indicates different diopter values at specific locations, these values being easily visually accessible by a user by simply looking at the tube. This scale extends along the outer tube 102 by being performed on a short side of said outer tube 102.

Referring to FIG. 12, the target 103 is mounted on a support 116 presenting a central cylindrical body 117, two short prominent parts 118 and two long prominent parts 119, 120. The target 103 is identical to a sheet of paper which would be circular-shaped. On one face of the target 103 are drawn patterns which are easily identifiable with an eye. On the particular example showed in FIG. 12, the patterns consist in a central circle 121 and in multiple radial lines 122 connecting an external edge 123 of the target 103 and said central circle 121. The central circle 121 and the lines 122 are rather dark, for example black, while the background is rather clear, for example white. Preferably the target 103 is bonded on a circular face of the central body 117 of the support 116, by means of an adhesive material, such as a glue. The two short prominent parts 118 are aligned along a diameter of the central body 117 by being placed on both sides of said body 117. The two long prominent parts 119, 120 are aligned along a diameter of the central body 117 by being placed on both sides of said body 117, said long parts 119, 120 being perpendicular to the short parts 118. One 120 of these long parts comprises a cylindrical portion 124 having an internal channel 125.

Figure 10:
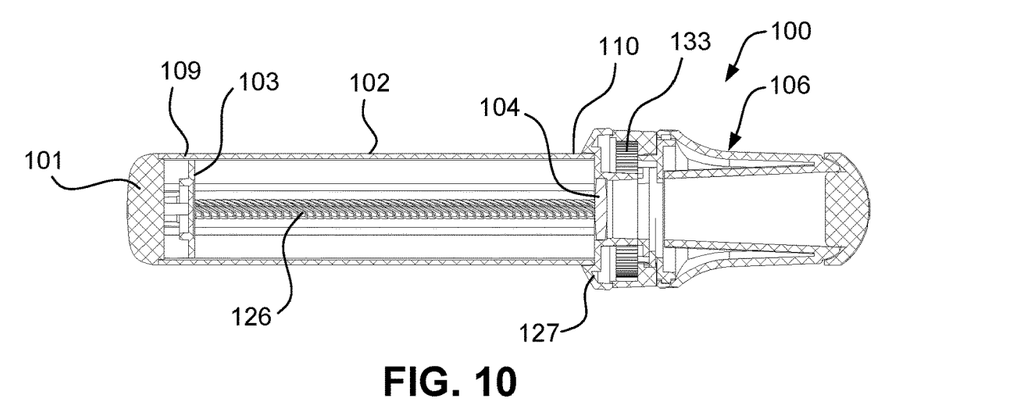
FIG. 10 is an axial longitudinal sectional view of the measurement device of FIG. 9A.

Referring to FIGS. 10 and 11, the support 116 of the target 103 is mounted in rotation on a threaded cylindrical rod 126 and can turn around the rod 126 by moving along said rod 126. This rod 126 has approximately the same length than the one of the outer tube 102, The support 116 is mounted on the rod 126 by passing said rod 126 through the internal channel 125 of the cylindrical portion 124 of one 120 of the two long prominent parts 119, 120 of said support 116.

The assembly comprising the rod 126 and the target's support 116 is placed inside the outer tube 102 so that the two long prominent parts 119, 120 are placed in the two long branches of the second long portion 114 of the cross section of the internal channel 112 of the outer tube 102, and the short prominent parts 118 are placed in the two short branches of the first short portion 113 of said cross section. In this way, the rod 126 extends along the outer tube 102 by being placed in one of the two long branches of the cross section of the internal channel 112 of the outer tube 102. With such an arrangement, if the rod 126 rotates about its revolution axis, since the support 116 cannot rotate inside the outer tube 102 due to the specific geometry of the cross section of its internal channel 112, the target 103 will move along the rod 126 without making any rotation by always keeping the same spatial orientation.

The measurement device 100 comprises an interface piece 127 having an enlarged cylindrical base 128 prolongated by a cylindrical hollow protrusion 129 having a smaller diameter than of said base 128, the revolution axis of said base 128 coinciding with the revolution axis of said protrusion 129. The lens 104 is mounted on the cylindrical hollow protrusion 129 so that the optical axis of said lens 104 coincides with the revolution axis of said protrusion 129. The lens 104 can be plane or curved. The enlarged base 128 is plane and has a raised peripheral edge 130. A pinion gear 131 is mounted in rotation on a face of the enlarged base 128, so that its rotation axis is perpendicular to the plane of said base 128. The pinion gear 131 interacts with the rod 126, so that a rotation of said pinion gear 131 leads to a rotation of the rod 126 about its revolution axis. The interface piece 127 is fixed to the second extremity 110 of the outer tube 102 by means of screws 111, so that the protrusion 129 comes inside the internal channel 112 of said outer tube 102.

A ring 133 having approximately the same external diameter than of the enlarged base 128, is mounted in the measurement device 100 so as to be in contact with the face of the enlarged base 128 on which the pinion gear 131 has been mounted. The ring 133 has an internal annular face 135 having notches all along its length, that is to say on 360°, and an external annular face 136 having reliefs all along its length, like for example grooves or ribs 134. These reliefs 134 aim to create a rugosity on the external surface 136 of the ring 133, allowing a user to easily make rotate the ring 133 with his hand. The internal face 135 with notches interacts with the pinion gear 131 by meshing. This ring 133 serves as a command button to control the movement of the target 103. Indeed, the ring 133 is free in rotation against the enlarged base 128 of the interface piece 127, and a user wishing that the target 103 be moved, turns the ring 133 with his hang, leading to the rotation of the pinion gear 131 and thus the rotation of the rod 126. Since the support 116 of the target 103 is locked in rotation due to the geometry and the size of the internal channel 112 of the outer tube 102, the target 103 can only move along the rod 126 and thus may get closer or away from the eye of the user.

Figure 9A:
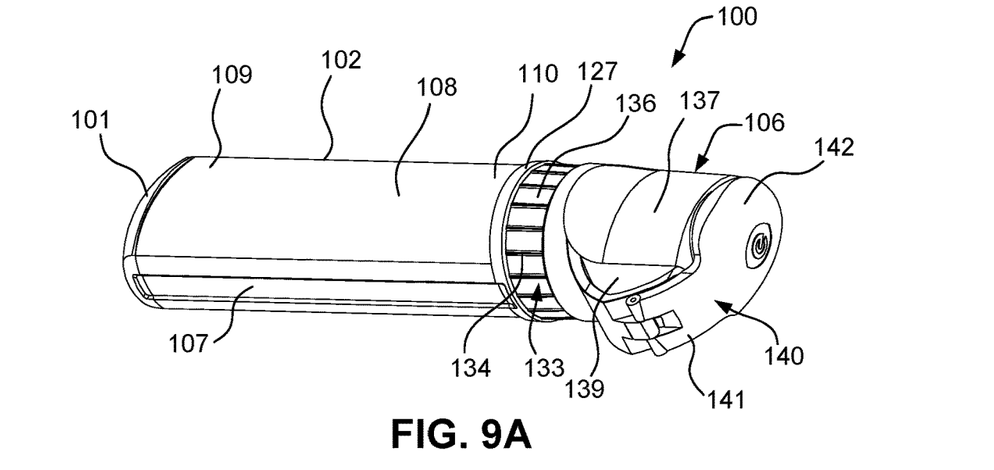
FIG. 9A is a perspective view of a preferred embodiment of a measurement device pursuant to the invention, the eyepiece cap being in a closing position.
Figure 9B:
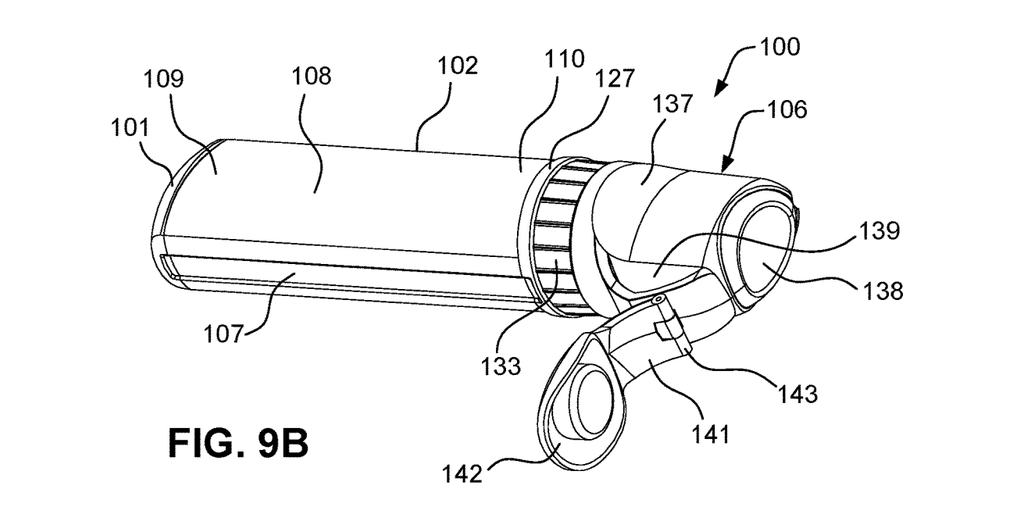
FIG. 9B is a perspective view of the measurement device of FIG. 9A, the eyepiece cap being in an opening position.

Referring to FIGS. 109A and 109B, the eyepiece 106 constitutes the most upstream part of the measurement device 100. It schematically comprises a cylindrical part 137 having an internal channel 138, and a lateral bulge 139 placed beside said cylindrical part 137.

Referring to FIGS. 9A and 9B, a cap 140 comprising an arm 141 and an enlarged head 142 is mounted in rotation on the lateral bulge 139 of the eyepiece 106, said arm 141 and said enlarged head 142 being in continuity and having the same curvature. This cap 140 looks like a spoon. A rotation axis 143 is fixed to the lateral bulge 139, and the arm 141 of the cap 140 is articulated mounted on this rotation axis 143. In this way, the eyepiece cap 140 can rotated about the rotation axis 143 between a closing position as shown in FIG. 9A for which the enlarged head 142 closes the internal channel 138 of the eyepiece 106, and an opening position as shown in FIG. 9B, for which it has rotated about 180° from the closing position and no more closes said internal channel 138. When the cap 140 is in the opening position, the enlarged head 142 serves to cover the eye of the user which is inactive during the test, that is to say, the eye which is not placed in front of the internal channel 138 of the cylindrical part 137 of the eyepiece 106. In this way the user does not have to close the inactive eye, improving the conditions for carrying out the test.

Referring to FIG. 11, the measurement device 100 implements locking means 144, 145 in order to maintain the target 103 in a given position along the rod 126, without any specific action of the user on said measurement device 100. These means involve a ratchet spring 144 and a ratchet holder 145. The ratchet spring 144 is wired and is annular-shaped. It corresponds to an open arc which extends between 220°, and 360°. The ratchet spring 144 is flexible and comprises a tooth 146 in a central position. It is solidarized to the ring 133 so that a rotation of said ring 133 leads to a simultaneous rotation of the ratchet spring 144, in the same direction and with the same amplitude. The ratchet holder 145 is fixed inside the measurement device 100 and comprises a series of notches regularly distributed along a curved surface of said ratchet holder 145. When the ring 133 is rotated, the spring also rotates, and the tooth 146 slides along the notches of the fixed ratchet holder 145 thanks to the flexibility character of the spring 144. When the ring stops rotating, the tooth 146 is locked in a notch of the ratchet holder 145.

Referring to FIG. 13, the measurement device 100 comprises an indicating means 160 comprising a pointing portion 147 and an indicator portion 115. The pointing portion is fixed to the support 116 of target 103 and is designed to move jointly with said support 116. This pointing portion 147 is a cursor which is arrow-shaped, and which slides along the outer tube 102 and more precisely along the indicator portion, which is represented by an outer scale 115 indicating different diopter values at specific locations along said outer tube 102. When a user moves the support 116, he moves simultaneously the cursor 147 along the scale 115.

The method of assessing the sight of a user with the preferred embodiment 100 of a measurement device pursuant to the invention disclosed before, comprises the following steps:

A step of catching with hand the measurement device 100,

A step of rotating the eyepiece cap 140 in order to place it in an opening position, A step of placing the measurement device 100 in front the eye of the user, of which the sight is intended to be tested, and more precisely, a step of placing the internal channel 138 of the cylindrical part 137 of the eyepiece 106 in front of said eye, to allow the user to see the target 103, A step of manually moving the target 103 along and inside the outer tube 102, through a manual rotation of the ring 133, until the user see clearly the target 103. The target 103 is locked at its place through the interaction between the ratchet spring 144 and the ratchet holder 145

A step of reading the diopter value on the outer scale 115 of the outer tube 102, which is indicated by the cursor 147.

The measurement device 100 can be made of plastic material. This plastic material can be transparent to allow the target to be continuously lighted by a natural lighting and thus to be more visible by the user. In another preferred embodiment, a small light can be included in the support 116 of the target and can be manually turns on in order to light the target 103 in dark weather.

The invention has been described above with the aid of embodiments without limitation of the general inventive concept.

Many further modifications and variations will suggest themselves to those skilled in the art upon referring to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A vision measurement device comprising:
   an eyepiece (20, 106), in which a lens (21, 104) is provided;
   an outer tube (30, 102) connected to the eyepiece (20, 106)) and in which a target (31, 103) having a predetermined pattern is provided, wherein the target (31, 103) is movable along an optical axis of the lens (21, 104)) with respect to the outer tube (30, 102);
   an indicating means (40, 160) for indicating diopter comprising an indicating portion (41, 115) and a pointing portion (42, 147) for indicating a diopter, wherein the indicator portion (41, 115) having a scale representing the diopter and the pointing portion (42, 147) indicating a value of the scale;
   wherein during the movement of the target (31, 103) with respect to the outer tube (30, 102) along the optical axis of the lens (21, 104), one of the indicator portion (41, 115) and the pointing portion (42, 147) moves along with the target (31, 103) with respect to the outer tube (30, 102) while the other of the indicator portion (41, 115) and the pointing portion (42, 147) does not move, and when an eye is capable of clearly seeing the predetermined pattern (121, 122) on the target (31, 103)) through the eyepiece (20, 106), the value of the scale indicated by the pointing portion (42, 147) corresponds to the diopter of the eye, and wherein,
   the target (103) is movable along the optical axis of the lens (104) inside the outer tube (102) by means of a mechanism involving:
   a threaded cylindrical rod (126) placed inside the outer tube (102) and on which the target (103) is mounted in rotation, a pinion gear (131) interacting with said rod (126) so that a rotation of said pinion gear (131) leads to the rotation of said rod (126) about its revolution axis, a notched ring (133) that interacts with the pinion gear (131) by meshing, so that a rotation of said ring (133) leads to the rotation of said pinion gear (131) thus leading to the rotation of the rod (126), and locking means (144, 145) preventing the target (103) to rotate relative to the rod (126) and allowing said target (103) to slide along said rod (126) by keeping the same spatial orientation.

2. The vision measurement device according to claim 1, wherein a rotation of the ring (133) in one direction leads to a movement of the target (103) in one direction along the rod (126), and wherein a rotation of said ring (133) in the other direction leads to a movement of the target (103) in an opposite direction along said rod (126).

3. The vision measurement device according to claim 2, wherein the notched ring (133) comprises an external surface (136) on which some reliefs (134) have been made so as to allow a manual rotation of said ring (133), and wherein the notched ring (133) comprises an internal surface (135) having notches intended to interact with the pinion gear (131).

4. The vision measurement device according to claim 2, wherein the outer tube (102) comprises an internal channel (112) having a cross section, and the locking means preventing the target (103) to rotate relative to the rod (126) is constituted by said internal channel (112) which will serve as a guide for said target (103) along the rod (126).

5. The vision measurement device according to claim 1, wherein the notched ring (133) comprises an external surface (136) on which some reliefs (134) have been made so as to allow a manual rotation of said ring (133), and wherein the notched ring (133) comprises an internal surface (135) having notches intended to interact with the pinion gear (131).

6. The vision measurement device according to claim 5, wherein the reliefs consist in a series of ribs (134) regularly spaced around the ring (133).

7. The vision measurement device according to claim 5, wherein the outer tube (102) comprises an internal channel (112) having a cross section, and the locking means preventing the target (103) to rotate relative to the rod (126) is constituted by said internal channel (112) which will serve as a guide for said target (103) along the rod (126).

8. The vision measurement device according to claim 1, wherein the outer tube (102) comprises an internal channel (112) having a specific cross section, and the locking means preventing the target (103) to rotate relative to the rod (126) is constituted by said internal channel (112) which will serve as a guide for said target (103) along the rod (126).

9. The vision measurement device according to claim 1, wherein the target (103) is fixed to a support (116) which is mounted in rotation on the rod (126), and wherein the target (103) is bonded to the support (116) with an adhesive material.

10. The vision measurement device according to claim 1, wherein the target (103) is circular-shaped and comprises patterns (121, 122).

11. The vision measurement device according to claim 10, wherein the patterns comprise a central circle (121) and a plurality of radial lines (122) connecting an external edge (123) of the target (103) to the central circle (121).

12. The vision measurement device according to claim 1, wherein the position of the target (103) along the rod (126) is locked by means of an interaction between a ratchet spring (144) solidarized to the notched ring (133) and a fixed ratchet holder (145).

13. The vision measurement device according to claim 1, wherein it comprises an eyepiece cap (140) articulated mounted on the eyepiece (106) between a closing position for which it closes an orifice (138) of said eyepiece (106) through which a user will look at the target (103), and an opening position for which it has rotated with an angle greater than 90°.

14. The vision measurement device according to claim 13 wherein the eyepiece cap (140) comprises an arm (141) and an enlarged head (142), and wherein said eyepiece (106) is articulated mounted at the level of said arm (141), the enlarged head (142) being intended to close the orifice (138) of the eyepiece (106).

15. The vision measurement device according to claim 1, wherein the indicator portion has a scale (115) representing the diopter and which extends outside and along the outer tube (102) parallel to the rod (126), and wherein the pointing portion (147) is a cursor which moves along the scale (115) simultaneously with the target (103).

16. The vision measurement device according to claim 1, further comprising:

an engagement means configurable to prevent the target from moving in one of the directions along the optical axis of the lens, and comprising:

a female ratchet (35) located on the end cap (34) of the outer tube (30), and a male ratchet (64) connected to the end cap of the inner tube (62) and rotating with the inner tube (60), wherein the male ratchet (64) is capable of engaging with the female ratchet (35) to prevent the inner tube (60) and the outer tube (30) from rotating with respect to each other in one direction, while allowing the inner tube and the outer tube to rotate with respect to each other in an opposite direction, wherein the end cap (62) of the inner tube (60) is capable of being pulled outwards to disengage the male ratchet (64) from the female ratchet (35) such that the inner tube (60) and the outer tube (30) is capable of being rotated with respect to each other in both the one direction and the opposite direction.

17. The vision measurement device according to claim 16, further comprising:

a restoring means configurable to restore the target to its initial position, and comprising:

a torsion spring, one end of the torsion spring being fixed to the inner tube (60) and the other end being fixed to the end cap (34) of the outer tube (30), and the torsion spring has restoring force only when the target leaves its initial position, wherein in the case that the target (31) leaves its initial position, when the end cap (62) of the inner tube (60) is pulled outwards, the inner tube (60) rotates with respect to the outer tube (30) due to the restoring force of the torsion spring, thereby moving the target (31) back to its initial position.

\* \* \* \* \*